(12) United States Patent
Johns

(10) Patent No.: US 7,320,459 B2
(45) Date of Patent: Jan. 22, 2008

(54) APPARATUS FOR DISPENSING A VAPOUR INTO AN AIR FLOW

(76) Inventor: Bradley Charles Johns, 21 Bronwyn Close, Bowral, New South Wales 2576 (AU)

( * ) Notice: Subject to any disclaimer, the term of this patent is extended or adjusted under 35 U.S.C. 154(b) by 307 days.

(21) Appl. No.: 10/488,141

(22) PCT Filed: Aug. 27, 2002

(86) PCT No.: PCT/AU02/01152

§ 371 (c)(1),
(2), (4) Date: Jul. 15, 2004

(87) PCT Pub. No.: WO03/019082

PCT Pub. Date: Mar. 6, 2003

(65) Prior Publication Data

US 2004/0238976 A1    Dec. 2, 2004

(30) Foreign Application Priority Data

Aug. 27, 2001 (AU) .................................... PR7285

(51) Int. Cl.
*B01F 3/04* (2006.01)
(52) U.S. Cl. .................. 261/142; 261/26; 261/30; 261/124; 261/DIG. 65; 261/DIG. 88; 261/DIG. 89; 422/124
(58) Field of Classification Search .......... 261/26, 261/30, 127, 142, DIG. 88, DIG. 89, 60, 261/121.1, 124, DIG. 65; 422/124
See application file for complete search history.

(56) References Cited

U.S. PATENT DOCUMENTS

| | | | | |
|---|---|---|---|---|
| 3,442,602 A | * | 5/1969 | Diehl | 422/4 |
| 4,166,087 A | | 8/1979 | Cline et al. | 261/96 |
| 5,651,942 A | | 7/1997 | Christensen | 422/125 |
| 6,371,451 B1 | * | 4/2002 | Choi | 261/26 |

FOREIGN PATENT DOCUMENTS

| | | |
|---|---|---|
| JP | 7016290 | 1/1995 |
| WO | WO 97/32611 | 9/1997 |
| WO | WO 00/37848 | 6/2000 |
| WO | WO 03/019082 | 3/2003 |

OTHER PUBLICATIONS

"Glade PlugIns"; Internet Ad; downloaded Jul. 12, 2004.

* cited by examiner

*Primary Examiner*—Robert A. Hopkins
(74) *Attorney, Agent, or Firm*—Gordon & Jacobson, PC

(57) ABSTRACT

An apparatus for dispensing a vapor of a liquid into a ventilation system includes a vessel for holding the liquid, a heater for heating the liquid in the vessel to form a vapor, and means for delivering the vapor into the air flow passing through a passageway of the ventilation system. The liquid may be an essential oil or other liquid. An aerator may be used to deliver the vapor into the air flow. The apparatus may also include one or more additional liquid reservoirs, a controller which regulates the operation of the heater in response to user control, an air flow detector, and data stored in a controller memory.

17 Claims, 3 Drawing Sheets

APPARATUS FOR DISPENSING A VAPOUR INTO AN AIR FLOW

BACKGROUND OF THE INVENTION

1. Technical Field

The present invention relates to air conditioning and other ventilation systems and more particularly to an apparatus and method of introducing essential oil vapours into an air flow of a ventilation system for health and deodorising purposes.

2. State of the Art

Building air conditioning, central heating and other ventilation systems are known to recirculate odours and microorganisms such as bacteria and fungi which may breed in the air passages of the ventilation system. It is believed that such microorganisms may be detrimental to the health and comfort of occupants of the building.

WO 88/00199 discloses a method of treating air conditioning system air by introducing a spray of oil of Melaleuca of a particular mean droplet size, and a spray composition comprising the oil dissolved in liquid carbon dioxide. However, there remains a need for a method and apparatus which relatively inexpensive, convenient and scaleable to suit large or small scale air conditioning or ventilation installations.

SUMMARY OF THE INVENTION

It is an object of the invention to provide an apparatus and method of introducing essential and/or fragrant oil vapours into the air flow of a ventilation system, so as to deodorise and/or disinfect the ventilation air, which meets some or all of these needs.

A first form of the present invention provides an apparatus for dispensing a vapor into an air flow of a ventilation system, said apparatus including
 a vessel for holding a liquid;
 a heater for heating the liquid in the vessel to cause evaporation of liquid in the vessel; and
 means for delivering vapor from said vessel into said air flow of the ventilation system.

Preferably, the apparatus further includes means for aerating said liquid to create gas bubbles therein. Preferably, said aeration means includes a gas tube located within said vessel, said tube having a plurality of gas holes therein and gas supply means in communication with said tube adapted to pump a gas through said holes to create said bubbles. Preferably, said gas is air.

In one preferred form, the apparatus further includes a user control interface remote from said vessel for user control of said apparatus, including switch means for said apparatus. Preferably, said user interface further includes input means for adjusting an amount of said vapor delivered to said air flow. Preferably, control means of the apparatus includes a temperature regulator which regulates said heating means responsive to the vapor adjustment input means by adjusting a temperature setpoint of the temperature regulator.

Preferably, the control means includes means for detecting a quantum of said air flow and adjusting evaporation of said liquid to maintain a desired concentration of said vapor in said air flow.

In a further preferred form, the apparatus includes a reservoir in communication with said first vessel for holding a supply of said liquid, and means for transferring said liquid from said reservoir vessel to said first vessel to maintain a predetermined level of said liquid in said first vessel.

Preferably, the apparatus includes a plurality of said vessels for holding different liquids and a user interface including user selection means for selective activation of heating means in said vessels. Preferably, said user selection means further selectively activates one or more valves closing off vapor delivery from those of said vessels containing liquids not selected by the user.

Preferably, said liquid is an essential oil or perfume. Preferably, said essential oil is Tea-tree (Melaleuca), Eucalyptus, pine or lemongrass oil, or blends thereof.

BRIEF DESCRIPTION OF THE DRAWINGS

Further preferred embodiments of the invention will now be described with reference to the accompanying drawings, in which.

DETAILED DESCRIPTION OF THE PREFERRED EMBODIMENTS

Figure 1:
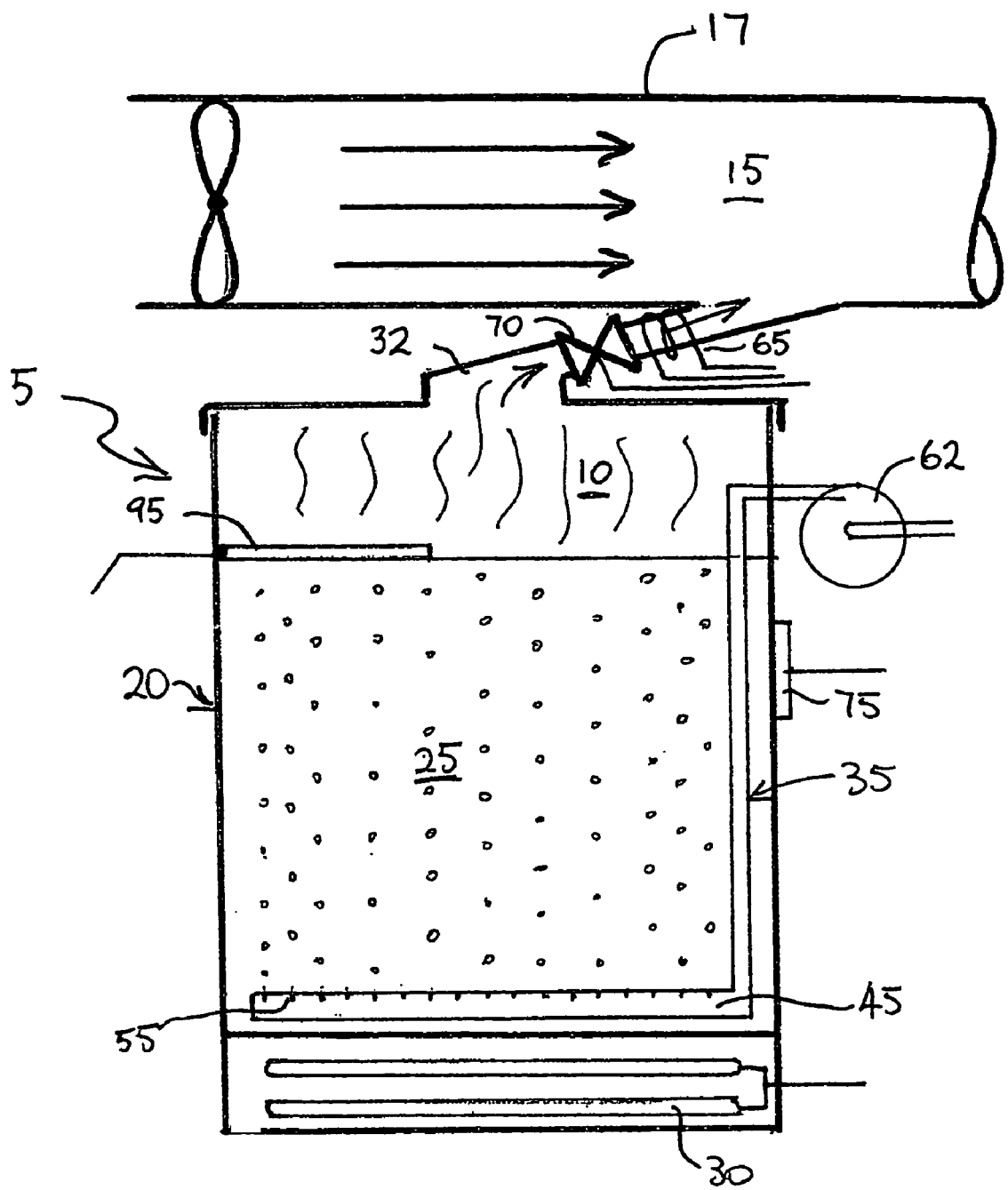
FIG. 1 is a schematic elevation of an oil vessel and delivery conduit apparatus according to a first embodiment of the invention.

FIG. 1 is a schematic depiction of an apparatus 5 for dispensing a vapor 10 into an air flow 15 flowing through an air passage 17 such as a supply or return air duct or plenum of a building ventilation system.

The apparatus is adapted for installation with a variety of central heating and ventilation system types, and air conditioning systems such as ducted air conditioning, split systems and rooftop packages. The apparatus may be installed with the original system installation, or retrofitted to an existing installation.

The apparatus of FIG. 1 includes a first vessel 20 for holding a predetermined quantity of an essential or fragrant oil 25, heating means 30 for heating the liquid in the vessel 20 to cause evaporation of the liquid from the vessel. The apparatus further includes a vapor delivery conduit 32 communicating between the head space above the liquid in the vessel and air passage 17. The apparatus will typically be installed in the roofspace of the building, adjacent to the evaporator of the air conditioning system, although in the case of a split system air conditioning unit may be incorporated in or attached to the evaporator (in cooling mode).

The apparatus further includes an aerator 35 for pumping bubbles of gas, typically air, through the oil 25 in the vessel 20. The aerator includes a tube 45 with perforations 55 therein, located at the base of the vessel 20. Aerator means 35 includes pump 62 adapted to pump air through an air hose into the tube 45. The air then passes through the perforations 55 to bubble the air through the oil in the vessel, to increase transfer of the oil vapor into the air flow 15. Preferably, there is provided a valve or other flow restriction means to adjust the aeration rate, for example from about 1 to 5 litres per minute, to help transport sufficient vapor to sustain a vapor concentration of from 1 to 10 PPM in a typical ducted air conditioning system.

The vessel 20 will preferably hold a predetermined volume, for example 1.0 litres, of an antimicrobial and aromatic essential oil or oil blend such as tea-tree (genus melaleuca) for deodorising, or pine, lemongrass and/or eucalyptus oils for helping relieve the symptoms of sinus congestion, colds or influenza, or essential oils or blends having aromatherapeutic properties such as a 'revitalising' oil or a 'calming' oil such as lavender.

The vessel preferably is constructed of corrosion resistant metal such as brass or stainless steel, or other material with good heat transfer properties, to facilitate transfer of heat from the heating element 30 into the oil in the vessel. The outside of the vessel is preferably insulated with a thick layer of polyester glass or similar insulative material to limit heat loss from the vessel in winter and heat gain in summer.

The vessel is fitted with an air-tight lid, with a connection to the vapor delivery conduit 32. The conduit slopes upward from the vessel to the duct, so that any vapor which condenses on the inside of the conduit wall will drain back into the vessel. A small wattage heating element 65 may also surround the delivery conduit to limit condensation in winter.

The lid, or the conduit, may further include a solenoid cut-off valve 70 for closing off delivery of vapor to the duct when the system is turned off, thus preventing unwanted evaporation of the oil. Furthermore, where the vapor is to be introduced into the higher pressure, supply side of the ventilation system, the conduit may also include a one-way check valve to prevent backflow.

The heater 30 includes one or more heater elements incorporated in the base of the vessel 20, so that the heat generated will rise through the oil in the vessel. The maximum wattage of the heater elements required will depend on the maximum oil vaporisation capacity, which in turn depends on the maximum air flow of the ventilation system to which the apparatus is installed, and the required oil vapor concentration. For a typical residential ducted air conditioning system, a heater power of 100-300 W can sustain an oil evaporation rate of approximately 5-25 g/hour, which is sufficient to produce a vapor concentration in the ventilation air flow of from 1-10 PPM.

The heater further includes a temperature sensor 75 inside or in heat transfer communication with the vessel, which regulates operation of the heater elements by switching off power to the heating elements when the desired oil temperature in the vessel is reached.

FIG. 2 schematically illustrates an installation of the system, including the control system for regulating the resultant concentration of oil in the recirculated air.

The illustrated apparatus includes an oil vessel 20 and delivery conduit arrangement, communicating with an air duct in the roofspace 80 of a building, generally as described above with reference to FIG. 1.

The system of FIG. 2 further includes an oil reservoir 85, typically of larger capacity than the first vessel, for example of 5-20 L, and an oil transfer pump 90 controlled by an oil level switch in the vessel, such as float switch 95. Upon the oil level in the vessel 20 falling below a predetermined level, the float switch causes operation of the oil transfer pump 90 to pump from reservoir 85 to the first vessel 20 until the level in the vessel again reaches the required level. In this way, a relatively constant oil level may be maintained in the first vessel, maintaining a constant length of the pathway of the bubbles through the oil so that the oil evaporation rate at the set temperature is predictable.

The reservoir 85 may be situated at a location accessible for refilling with oil, and may include an inlet hose 92 leading to a filler plate 93 with a filling port 95 mounted on a wall of the building or at some other convenient location.

Operation of the system is regulated by a central control processor 100 connected to a the electricity supply. The functions of the controller will be described in more detail below.

The controller has inputs for receiving data from a memory device 105, the temperature sensor 75, float switch 95, an air flow sensor 110 which detects air velocity in the duct 17, a system maintenance control interface 115 and a user control interface 120.

The controller has outputs for controlling operation of the air pump 62, heating elements 30 and 65, solenoid valve 70, and oil pump 90.

The air flow sensor 110 is preferably a hot-wire anemometer or similar which measures the duct air velocity in m/s, from which the volume of air flow may be calculated.

The maintenance interface 115 is adapted for initial set-up and subsequent adjustment of the system by a technician and has a wide range of functionality. Typically, the maintenance interface will be situated either in the roofspace 80 with the controller 100 or portable so that the technician can carry a single maintenance interface device such as a personal display device to service a number of installations.

The user interface will typically be remote from the controller and vessel, and be mounted on an internal wall 125 of the building space, readily accessible by the occupants of the air conditioned space. The user interface has a limited functionality. For example, in the illustrated embodiment the user interface has an on-off switch and a vapor concentration adjustment control 130. The user interface may further include an oil selection switch for selecting between oils, as will be described later with reference to FIG. 3, and a timer for pre-programming operation of the system for example to run the system for an hour before the occupants are due to arrive home of an evening.

In use, the memory device 105 of the controller 100 is programmed with empirical evaporation rate against vessel temperature data for the type of essential oil or oils to be placed in vessel 20. Typically, over the temperature range over which the apparatus is to used, the relationship will be sufficiently linear to be approximated by a line of best fit according to the formula:

$$R=MT+B,$$

where R is the evaporation rate in grams/hour,

T is the vessel temperature in ° C., and

M and B are coefficients.

The relationship between the evaporation rate and temperature for a particular type of oil may thus be derived by the controller from values of M and B stored in the controller memory.

Also entered in the controller memory by the technician is the air duct diameter, from which the cross-sectional area of the air duct, so that the air flow volume may be derived by multiplying the air flow velocity by the calculated cross-sectional area of the duct Using the maintenance interface, the technician sets a baseline vapor concentration setpoint for the system, in parts per million. The user interface 120 includes a control knob 130 which allows user controlled variation of the vapor concentration up to a certain maximum percentage, for example 100%, above or below the setpoint.

When the system is switched on at the user interface, the controller uses the baseline vapor concentration, as modified by the user control knob setting, and the air flow volume calculated from the air flow sensor reading to calculate the required oil evaporation rate from the vessel. The controller then uses the stored correlation between evaporation rate and temperature to derive a vessel temperature setpoint, and controls the vessel heating element according to feedback received from the temperature sensor to maintain the required temperature. Typically, the vessel will be operated at a temperature range of about 40-70° C., for example 50-60° C., to maintain a vapor concentration of about 1-5 PPM, at which concentration the vapor will produce a subtle but pleasant fragrance. The air pump 62 is activated and solenoid valve 70 opened to allow the vapor to be transported into the air duct and thus distributed through the building space.

If the vessel temperature is above the setpoint, as may be the case in summer where roofspace temperatures can reach 70° C., the controller will turn off the air pump to reduce the transport of vapor into the air duct.

When the oil level in the vessel drops sufficiently to actuate the level switch 95, the controller activates the reservoir oil pump 90 to top up the oil level in the vessel 20.

EXAMPLE

Figure 2:
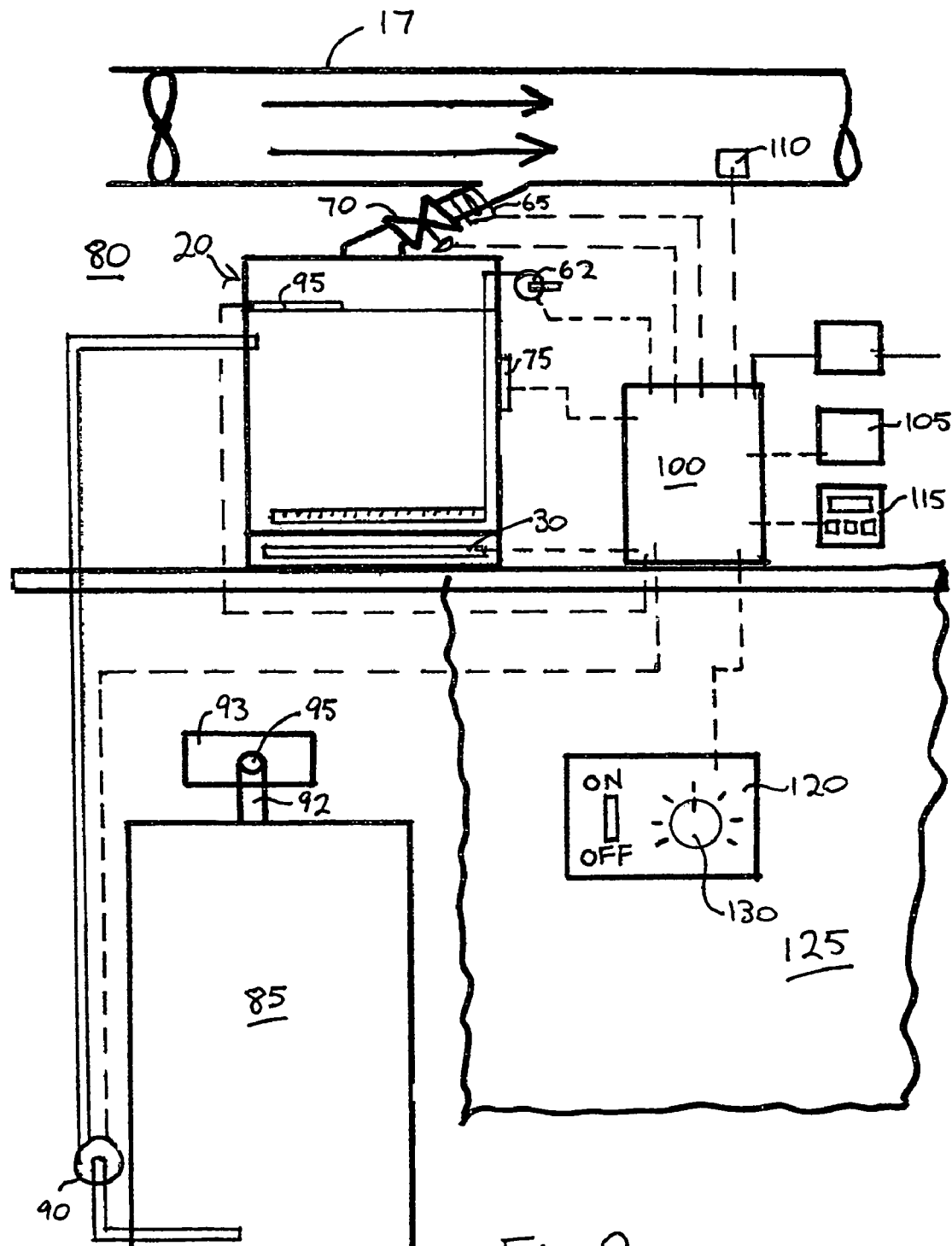
FIG. 2 is a schematic illustrating an installation of the vessel and associated control apparatus.

An example illustrating the control parameters of the controller and the maintenance and user interfaces of FIG. 2 are further described below.

The maintenance interface allows the continuous interrogation of the controller state and the configuration of the controller to the particular requirements of the site at which it is installed. The maintenance interface is accessed through a portable display device having on/off, menu advance/select, up and down control keys, and an 'alert' light. The display device may be connected/disconnected from the scent controller at any time.

Within the controller, each operational parameters is assigned a unique address. The current value of a single parameter may be viewed by selecting its address upon the display device. Parameters which form part of the controller's configuration may be changed by the technician. The new value will take effect when the address is advanced/altered to display a different parameter.

Parameters which display current state information, measured values or values derived from measurements, are not able to be changed by the user. These values are continually updated as conditions within the controller change.

Alteration of the parameter address is effected by selecting the menu advance key while operating the up and down keys. Alteration of the configuration parameter values is effected by operating the up and down keys while the desired address is being displayed. If these keys are selected for an extended period, a "repeat" function is activated, causing the value to rapidly increase/decrease. Increases/decreases to the parameter value will not be possible if the value has reached its respective maximum/minimum value.

The maintenance controller has the following "error states". When an error is detected, the unit discontinues operation and flashes the "Alert" light on the interface control panel. Operation can be restored by the user selecting the "Off/On" button.

When an error is encountered, if the maintenance interface is not currently modifying a value, the address is forced to the "error" address. The error states are as follows:

0. No Fault

The system is operating normally.

1. Fluid Level

The correct fluid level could not be achieved within the nominated period. This is not considered to be a "serious" fault and is distinguished by illuminating the "Alert" light, but not flashing it.

2. Lost Configuration

The system internally stores all configuration parameters within a semi-permanent storage area. In the case of a serious malfunction, this memory can become corrupt. In the absence of valid configuration information, the controller is unable to function. This fault can only be cleared by operating the maintenance interface up and down keys (thus demonstrating that the parameters have been reviewed and reset).

3. Airflow Sensor

The airflow sensor has been unable to make a correct airflow measurement. This is probably due to a wiring/sensor fault, or possibly due to dirt accumulation on the sensor.

4. Heater

The system is unable to correctly control the fluid chamber temperature. This is probably due to a fault in the heater or temperature sensor. It may possibly be die to an excessive ambient temperature.

Display parameters which are available for display only, and their addresses are as follows:

0. Chamber Temperature

The current temperature of the fluid chamber, expresses in ° C.÷10, i.e. the display shows XX.X ° C.

1. Chamber Setpoint

The fluid chamber temperature which the controller is trying to achieve, expressed in ° C.÷10, i.e the display shows XX.X ° C. If the heater is not currently active, the value 0 is shown.

2. Fault Indication

The system error state value (see the discussion of the errors above), or 0 if there is no error.

3. Airflow

The current airflow reading, expressed in m/s÷10, i.e. the display shows XX.X m/s. If the airflow sensor is currently inactive or has not been active for a sufficient time to produce a stable reading (typically about 1 minute), the value 0 is displayed.

The airflow sensor is activated when the system is "On" i.e. the user interface "Active" light is steady red or green. The airflow sensor also activated when the system is in "Service" mode (see below).

4. Knob Reading

The setting of the user control panel knob, expressed as a value from 0 to 100.

5. Air Volume

The current air volume reading (the amount of air passing the airflow sensor each second), expressed in 1/sx10, i.e. the display shows XXX01/s (where XXX are the display digits). If the airflow sensor is currently inactive or has not been active for a sufficient time to produce a stable reading (typically about 1 minute), the value 0 is displayed.

This value is derived by combining the air velocity measurement with the configured duct diameter.

6. Derived Scent Concentration

The scent concentration which the controller will attempt to maintain within the airstream, expressed in PPM÷100 i.e. the display shows X.XX PPM.

This value is derived by combining the "Baseline Scent Concentration" with the setting of the user control panel knob. The knob setting allows a ±30% variation to the "Baseline Scent Concentration".

7. Evolution Rate

The rate at which the controller is attempting to evaporate fluid from the chamber, expressed in g/h÷10, i.e. The display shows XX.X g/h.

This value is derived from the "Derived Scent Concentration" and the mass of the air passing through the system (which is derived from the air volume and the known density of air).

The parameters which configure the operation of the system and are available for modification, are as follows:

8. Service Setpoint

If this value is set to a non-zero value, the system enters a "service mode", in which the "Chamber Setpoint" is fixed at the value defined by the service setpoint. This value is expressed in ° C.÷10, i.e. the display shows XX.X ° C. This value can range from 0 to 99.9° C.

While service mode is active, the fluid pump will not operate and the user control panel flashes both lights.

9. Duct Diameter

This value defines the diameter of the duct at the point where the airflow measurement is being taken, expressed in cm, i.e. the display shows XXX cm. This value can range from 0 to 225 cm.

The duct is assumed to be round. If a different cross section is being used, it must be converted to an equivalent circular cross section.

10. Baseline Scent Concentration

The scent concentration which is configured for this site, expressed in PPM÷100, i.e. the display shows X.XX PPM. This value can range from 0 to 99 PPM, though in practice will typically range from about 1-10 PPM.

This value is modified by the setting of the "user control panel knob" to yield the actual scent output (see "Derived Scent Concentration" above).

11. Fluid M Coefficient
12. Fluid B Coefficient

These parameters define the evaporation characteristics of the scent fluid which is being used, as previously described. These values can range from 0 to 225 and 0 to 999 respectively.

These values are specific to the fluid being used and are determined by previous testing of the fluids.

13. Chamber Fill Timeout

The amount of time which the controller will allow the fluid pump to run, after which a "fluid level" error is declared. This value is expressed in minutes÷10, i.e. the display shows XX.X minutes. This value can range from 0 to 50.0 minutes.

14. Chamber Run Temperature Range

This defines how close the oil vessel temperature must be to the "Chamber Setpoint" before it is considered to the "at temperature". The vessel temperature must fall within this range before the air pump will operate.

This value is expressed in ° C.÷10, i.e. the display shows XX.X ° C. This value can range from 0 to 25.5° C.

15. Airflow Calibration M
16. Airflow Calibration B

These parameters define the characteristics of the airflow sensor and are specific to the sensor which is attached to the system. These values can range from 0 to 255 and 0 to 999 respectively.

Each sensor is labelled with these values during production testing.

17. Chamber Temperature Calibration

This parameter defines the characteristics of the controller and temperature sensor in combination. This value can range from 0 to 100.

Each system (consisting of a controller and temperature sensor is labelled with this value during production testing.

Figure 3:
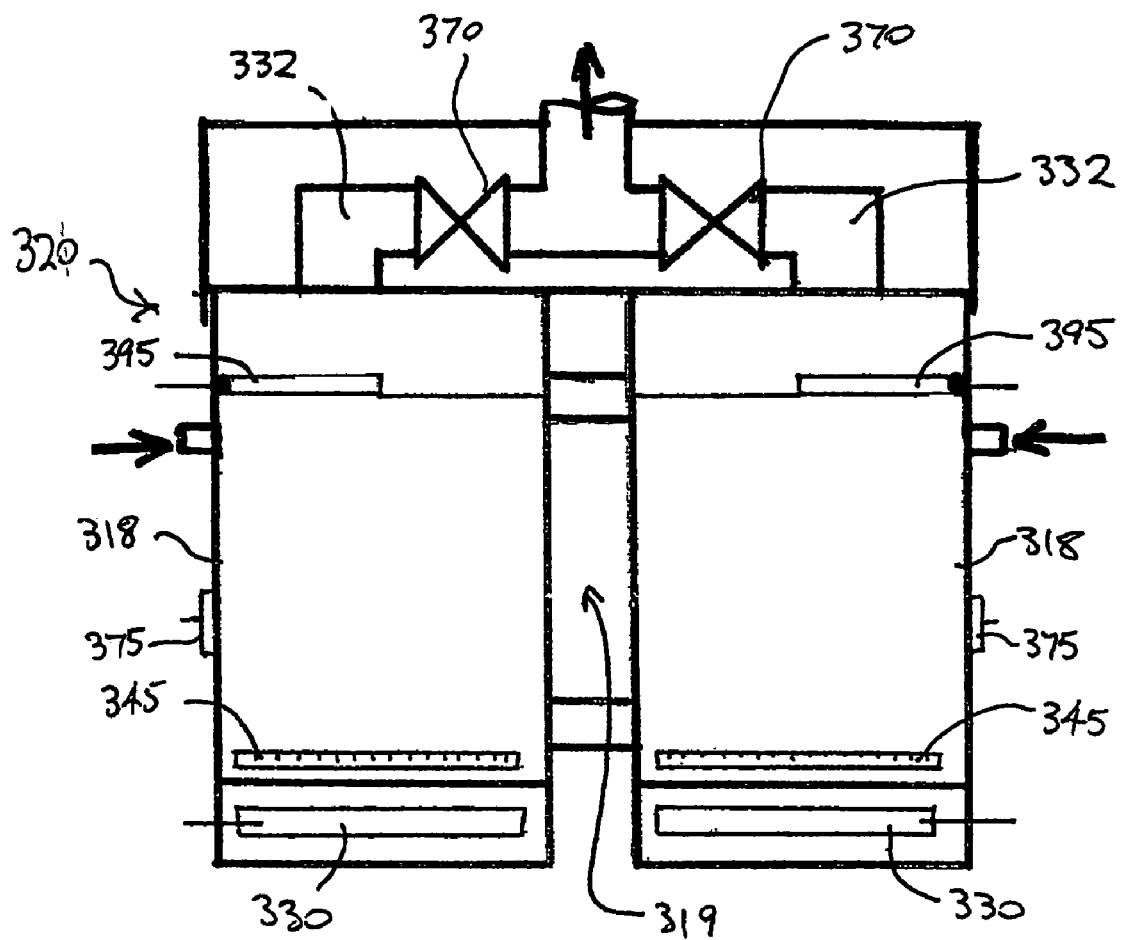
FIG. 3 is a schematic elevation of a multi-compartment oil vessel according to a second embodiment.

FIG. 3 illustrates an alternative vessel arrangement adapted to allow for user multiple oils to be used in the system.

The vessel 320 of FIG. 3 is formed as two or more separate oil chambers 318 separated by an air gap 319 or insulation material (not shown) to prevent substantial heat transfer between the chambers. Each chamber has its own heating elements 330, air tube 345, temperature sensor 375 and level switch 395, controlled by the controller. Each chamber will also have its own reservoir vessel and oil pump(not shown). Separate air pumps, or a single air pump with means for switching between chambers, may be used.

Each chamber may have a separate lid or, as illustrated, the vessel lid may comprise a vapor manifold with passages 332 communicating with respective of the chambers, each with its own solenoid valve 370.

It is envisaged that the chambers will be filled with oils of different scents and characteristics, for example a 'invigorating' oil in one chamber and a 'relaxing' oil in the other. The user interface will have a switch allowing the user to select which of the oils is to be distributed, so for example the user may select the invigorating oil in the early evening when arriving home from work, and select the relaxing oil later in the evening.

The controller will be programmed with the M and B values for the oils in each of the chambers, and will selectively operate the chamber corresponding to the oil selected at the user interface, in the manner previously described. The solenoid valves for the other chambers will remain closed.

It is envisaged that a typical installation will be set to a trace vapor concentration, for example 1-5 PPM, at which the scent is just detectable, and in typical residential installations might be run for only a few hours per day. However, in commercial establishments it may be desirable to run the system full time at somewhat higher concentrations to counteract odours such as cigarette smoke.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. Apparatus for dispensing a vapour into an air flow of a ventilation system, said apparatus including:
   a vessel for holding a liquid;
   a heater for heating the liquid in the vessel to cause evaporation of liquid in the vessel;
   an apparatus for delivering vapour from said vessel into said air flow of the ventilation system; and
   an aerator for aerating said liquid to create gas bubbles therein.

2. Vapour dispensing apparatus according to claim 1, wherein said aerator includes a gas tube located within said vessel, said tube having a plurality of gas holes therein and a gas supply in communication with said tube adapted to pump a gas through said holes to create said bubbles.

3. Vapour dispensing apparatus according to claim 2, wherein said gas is air.

4. Vapour dispensing apparatus according to claim 3, including means for adjusting the rate at which said gas supply pumps the air.

5. Vapour dispensing apparatus according to claim 1, further including a user control interface remote from said vessel for user control of said apparatus, including a switch for said apparatus.

6. Vapour dispensing apparatus according to claim 5, said user control interface further including a vapor adjustment input for adjusting an amount of said vapour delivered to said air flow.

7. Vapour dispensing apparatus according to claim 6, including a controller including a temperature regulator which regulates said heater responsive to said vapour adjustment input.

8. Vapour dispensing apparatus according to claim 7, wherein said controller adjusts a temperature setpoint of said temperature regulator.

9. Vapour dispensing apparatus according to claim 1, including a controller including apparatus for detecting a quantum of said air flow and adjusting evaporation of said liquid to maintain a desired concentration of said vapour in said air flow.

10. Vapour dispensing apparatus according to claim 1, further including a reservoir in communication with said vessel for holding a supply of said liquid, a level detector for detecting a liquid level in said vessel and apparatus for transferring said liquid from said reservoir to said first vessel to maintain a predetermined level of said liquid in said vessel.

11. Vapour dispensing apparatus according to claim 1, wherein said liquid is an essential oil or perfume.

12. Vapour dispensing apparatus according to claim 11, wherein said liquid is an essential oil selected from tea-tree (Melaleuca), Eucalyptus, pine or lemongrass oil, or blends thereof.

13. Vapour dispensing apparatus according to claim 1, wherein said air flow is in an air passage of an air conditioning system.

14. Apparatus for dispensing a vapour into an air flow of a ventilation system, said apparatus including:
a plurality of vessels for holding different liquids;
a heater for heating the liquids in the vessels to cause evaporation of the liquid in the vessel;
apparatus for delivering vapour from said vessels into said air flow of the ventilation system;
aerator for aerating said liquids to create gas bubbles therein; and
a user control interface including user selection apparatus for causing selective activation of said heater.

15. Vapour dispensing apparatus according to claim 14, wherein said user selection apparatus further selectively causes activation of one or more valves closing off vapour delivery from those of said vessels containing liquids not selected by the user.

16. A method of dispensing a vapour into an air flow of a ventilation system, including the steps of:
providing a vessel holding a liquid to be vaporised;
heating the liquid in the vessel to cause evaporation of liquid in the vessel;
delivering vapour from said vessel into said air flow of the ventilation system; and
aerating said liquid in the vessel to create bubbles therein.

17. A method according to claim 16, further including adjusting the temperature of the liquid in said vessel to control a concentration of vapour in said air flow.

* * * * *